United States Patent [19]

Chu

[11] Patent Number: 4,689,399
[45] Date of Patent: Aug. 25, 1987

[54] COLLAGEN MEMBRANES FOR MEDICAL USE

[75] Inventor: George Chu, Sunnyvale, Calif.

[73] Assignee: Collagen Corporation, Palo Alto, Calif.

[21] Appl. No.: 840,312

[22] Filed: Mar. 13, 1986

Related U.S. Application Data

[62] Division of Ser. No. 685,350, Dec. 24, 1984, Pat. No. 4,600,533.

[51] Int. Cl.$^4$ .......................... C07G 7/00; A61L 15/04
[52] U.S. Cl. ...................................... 530/356; 128/156; 128/DIG. 8; 428/473
[58] Field of Search ................. 530/356; 128/82, 155, 128/156, DIG. 8; 428/473

[56] References Cited

U.S. PATENT DOCUMENTS

| | | | |
|---|---|---|---|
| 2,934,446 | 4/1960 | Highberger et al. | 530/356 |
| 4,233,360 | 11/1980 | Luck et al. | 530/356 |
| 4,242,291 | 12/1980 | Hughes et al. | 264/1 |
| 4,412,947 | 11/1983 | Cioca | 424/116 |
| 4,453,939 | 6/1984 | Zimmerman et al. | 604/368 |
| 4,505,855 | 3/1985 | Bruns et al. | 128/DIG. 8 |

FOREIGN PATENT DOCUMENTS

| | | |
|---|---|---|
| 0089152 | 9/1983 | European Pat. Off. |
| 92200 | 10/1983 | European Pat. Off. |
| 49-039174 | 6/1974 | Japan |

Primary Examiner—Morton Foelak
Assistant Examiner—Nathan M. Nutter
Attorney, Agent, or Firm—Ciotti & Murashige

[57] ABSTRACT

A process for preparing collagen membranes useful in tissue repair, and wound healing and related membranous implant materials useful in both hard and soft tissue applications is disclosed. The resulting membranes and materials have properties which can be varied as desired to suit intended use. Variation results from altering the precise conditions of formation of the membrane or of related fibers and solids. The process comprises first forming a gel from solubilized collagen, followed by converting the gel into a one-, two- or three-dimensional membranous solid form. This conversion is performed either by applying pressure to the gel, or by disrupting the gel and separating the resulting precipitate for casting.

7 Claims, 2 Drawing Figures

COLLAGEN MEMBRANES FOR MEDICAL USE

This application is a division, of application Ser. No. 685,350, filedDec. 24, 1984 and now U.S. Pat. No. 4,600,533.

TECHNICAL FIELD

The invention relates to the field of materials useful for repair of tissue and relevant to wound healing. More precisely, the invention relates to a collagen membranous material prepared by a novel process, which membranes are biocompatible, non-inflamatory, and useful in the repair of tissue as artificial implants.

BACKGROUND ART

Numerous attempts have been made to obtain artificial membranes which can be used as substitutes for skin, blood vessels, ligaments, or other connective tissue. Many of these membranes utilize collagen, as collagen is the major component of connective tissue in general. An extensive literature exists with respect to methods for preparing such membranes, either of collagen alone, (see, for example, U.S. Pat. No. 4,412,947; Japanese Pat. No. 74/039174; and U.S. Pat. No. 4,242,291) or of collagen in combination with other materials (see, e.g., U.S. Pat. No. 4,453,939). Other membranes use combinations of materials such as glycoproteins with fibrinogen and thrombin (EPO Application Publication No. 92200, published Oct. 26, 1983), and a combination of keratin derived and glucosaminoglycan polymers (European Patent Publication No. 89152, published Sept. 21, 1983).

The properties and quality of the resulting membranes with respect to physical characteristics useful in the particular application intended, and their biological characteristics, such as biocompatability, stability, and integration with surrounding tissue are determined by the nature of the material, e.g., the nature of the collagen used to form the membranes, and on the process used in their formation.

The membranes in the art have had variable success for their intended uses, which include cornea replacements, artificial skin, and wound healing. Many cause inflamation, and have less than optimum properties of flexibility, biological stability, and strength.

The present invention offers a process whereby desirable properties can be obtained in the resulting membrane through the use of non-immunogenic collagen formed into a membranous material by a spectrum of processes which offer flexibility in the physical properties of the product, so as to permit these properties to be adapted to intended use. The membranous material can be used as a two-dimensional membrane, shaped into a three-dimensional implant, or formed into a one-dimensional fiber.

DISCLOSURE OF THE INVENTION

The invention provides collagen membranes whose physical properties are designed to be suitable for uses in a variety of medical applications including blood vessel repair, uterus repair, reconstruction of lumen surfaces, tendon replacements, and artificial skin. The membranes may also be used as substrates for production of desired cell cultures in vitro. The properties of the membrane are determined by appropriate selection from a spectrum of preparation processes so as to obtain to those characteristics appropriate for a selected use. Similar flexibility is available in the properties of the one- and three-dimensional constructs prepared by modification of, or additions to, the membrane preparation process. The resulting fibers are useful as replacement materials for tendons or ligaments, and the three-dimensional blocks or solids provide implants for use in tissue repair or wound-gap closure.

Thus, in one aspect, the invention relates to collagenous membranous materials which are prepared by the general process of obtaining a gel from a solution of collagen, and converting the gel into membrane form. In another aspect the invention relates to fibers or solids prepared from the gel. In still another aspect, the invention relates to the general process itself, and to the specific methods used within the context of this general process to obtain two-dimensional membranes, fibers, and solids of desired properties.

The gel may be obtained from solubilized collagen by three alternative approaches. In one approach, the solution of collagen is treated with a precipitating buffer which insolublizes the collagen by raising the pH. In this approach, both collagen and buffer solutions are pre-cooled almost to freezing, mixed, and then allowed to incubate at approximately room temperature to induce gel formation. In a second approach, the above mixture is centrifuged, rather than incubated without gravitational pressure, and the supernatant from the centrafugation is recovered and allowed to incubate at approximately room temperature. In a third approach, the solution of collagen is treated with an insolublizing solution at ambient temperature, and the insolublizing solution is designed to bring the mixture to physiological pH and ionic strength. The mixture is then allowed to incubate at approximately 37° C. to create the gel. The third approach may be modified by degassing the mixture immediately upon mixing, and placing the degassed mixture into a mold before incubation.

The conversion of the gel to a membrane may also be accomplished by two basic alternative approaches. In one approach, the gel is compressed under constant pressure to form a mat which is then dried. Using this method, in addition to obtaining two-dimensional membranes, a solid implant may be prepared directly by compressing the molded gel obtained from the modification of the gel formation process wich employs degassing. A fiber product is obtained if the pressure is applied around the circumference of a cylinder formed from the gel. In the second approach, the gel is disrupted, the disrupted gel centrifuged to obtain a precipitate, and the precipitate cast into molds and dried. Depending on the dimensions and shape of the mold, either a membrane or solid can be obtained.

MODES OF CARRYING OUT THE INVENTION

Figure 1:
FIG. 1 is an electron micrograph at 30,000 times magnification of a collagen membrane prepared by the process of forming a collagen gel (by neutralizing collagen in solution at room temperature to form the gel) and compressing the gel at constant pressure.

The process of the invention starts with a collagen in solution. Collagen may be solubilized and purified from mamalian connective tissue, and has been prepared from bovine skin, porcine skin, and mammalian bone, along with a number of other sources. Collagen may be solubilized by disrupting the fibers in acid, as is well known in the art. Indeed, collagen in solution (CIS) is commercially available, conveniently, under the trademark Zygen ® from Collagen Corporation, Palo Alto, Calif.

Native collagen exists in a fibrillar form which results from the triple helical structure of the peptide chains. The helical structure is generated by virtue of repeating triplet sequences composed of glycine linked to two amino acids, commonly proline and hydroxyproline in the amino acid sequence. The regions of these triplet repeating units aggregate themselves into triple helical structures. In addition, all collagen chains contain regions at each end which do not have the triplet glycine sequence and are thus not helical. These regions are thought to be responsible for the immunogenicity associated with most collagen preparations, and are called telopeptides. The immunogenicity of a collagen preparation can, in large part, be mitigated by removal of these telopeptides to produce "atelopeptide collagen". The removal is accomplished by digestion with proteolytic enzymes such as trypsin or pepsin. The non-helical telopeptide regions are also required to form the cross-links which are responsible for stability of the fibrillar structure in the native material. Atelopeptide collagen must be cross-linked artificially, if it is desired to obtain this characteristic.

The collagen in solution which forms the starting material for the process of the invention is preferably an atelopeptide collagen, such as Zygen ® CIS. The cross-linking of the collagen in the resulting membranous material is optional, but can effected by treating the membranous material with glutaraldehyde to obtain the desired cross-links. Procedures for this cross-linking are known in the art, and are described in detail in U.S. Ser. No. 663,478, filed Oct. 22, 1984 and now U.S. Pat. No. 4,582,640, assigned to the same assignee, and incorporated herein by reference. Briefly, the material is treated with a solution containing 0.05-1% glutaraldehyde for 1-16 hours, and then quenched by addition of a glycine solution to a concentration of about 0.1-0.4M glycine. The cross-linking solution is then removed by washing.

The process of the invention for forming collagen membranes or related membranous materials, comprises, basically, two steps: the formation of a gel from a collagen in solution, and the conversion of the gel to the membrane or other desired form.

Each of these processes may be performed in a spectrum of temperature, gravitational, and ionic strength conditions, and the intermediate solutions may or may not be degassed, and the resulting product will have properties which vary accordingly. The temperature at which gel formation takes place may be between approximately 4° C. and approximately 37° C.; the ionic strength may vary between about 0.05 to about physiological ionic strength, and the gravitational field conditions may vary from $1 \times g$ to about $13000 \times g$. The exemplary processes set forth below typify the extremes of these variables, and it is understood that intermediate cases may also be useful, depending on the nature of the membrane desired. Degassing and molding prior to formation of the gel appears to result in a tougher product, which can be further manipulated to form a fiber, membrane or solid.

The conversion of the gel to a membrane may be effected in two basically different ways: either by compressing the gel to squeeze out liquid, and form a more cohesive "mat", followed by drying in air; or by disrupting the gel matrix, centrifuging the disruptate to recover a precipitated collagen, homogenizing the precipitate into a past, and casting the paste with a mold.

The nature of the properties of the resulting membrane depends greatly on which of these two conversion processes is used; the product of the compression process is flexible, translucent, and smooth, and forms a film-like material with relatively high tensile strength. The product of disrupting the gel followed by precipitation of the disruptate, is relatively brittle and semi-transparent, has a rough surface, and is relatively thick.

Either membrane, however, can be characterised as a random fibrillar network wherein the fibrils are approximately of the diameter 70-300 nanometers, and approximately $0.5-5\mu$ in length.

For the compression process, the gel is squeezed in a suitable piston type device, such as, for example, the apparatus presently used to obtain cakes of tofu. Compression is conducted at approximately room temperature by using the collagen gel in situ in the medium in which it was prepared. The compression is applied using 1.1-3 atmospheres pressure, and continued until the volume is approximately less than 5% of the original gel. The resulting flat collagen fiber mat is then dried in air at a low temperature (less than about 37° C.) to obtain the desired membrane. It is also desirable to wash the remaining salts from the membrane. The washing can be effected by washing with water, and redrying, again in air, at low temperature.

The process which utilizes disruption of the gel typically is conducted by mechanically disrupting the matrix, such as with a spatula, followed by centrifugation at approximately $13000 \times g$ for about 20-30 minutes to obtain the precipitate. The precipitate is then homogenized sufficiently to form a paste-like material, at room temperature, and the paste is cast into a mold and allowed to set in air at low temperature (below about 37° C.). The dried material is then desalted, if desired, by washing in water, and redrying in air.

The resulting materials may be employed in the soft tissue repair constructions ordinarily utilizing artificial membranes, such as burned skin replacements, tendon reconstruction, or wound repair. They may also be shaped into various forms and used in connection with hard tissue repair. The cast or compressed membranes may be reformed into three dimensional objects for implantation in replacing sections of bone by rolling into cylinders, or by stacking and cutting to shape. The membranes may also be used in their two dimensional configuration by successively packing the membranes into a defect, such as a cranial or peridontal cavity. In general, onlay type repair may be done by stacking these membranes into the cavity.

Three dimensional implants are also obtainable directly from the gel by compression into an appropriate mold. In this method of construction, it is preferred that the mixture containing the CIS and precipitating buffer be degassed and molded prior to compression. (Degassing may be used in the related processes which result in membranes and fibers, also). The dense collagen fiber network which is formed by compression of the degassed, molded collagen gel is dried, desalted by washing, remolded before redrying, and, if desired, aged at elevated temperature to encourage residual cross-linking. In addition, fibers can be formed preferably directly from the gel before compression or disruption. The gel is wrapped in a porous, absorbent material and squeezed or rolled into the desired diameter fiber. The disrupted gel may also be used, but in this event fibers must be formed by casting and stretching, and the process is more cumbersome, leading to a less desirable product.

The following examples are intended to illustrate, but not to limit the invention. The first three examples represent alternative methods of forming the gel, combined with the compression method for forming a membrane; examples 4-6 represent similar gel forming methods, followed by membrane formation using the disruptate. Examples 7 and 8 illustrate formation of cross-links in the resulting membranes whether formed by compression or disruption and precipitate recovery. Example 9 shows the use of degassed and molded mixtures in gel formation where the gel is used directly in forming a three dimensional implant.

EXAMPLE 1.

90 ml Zygen ® CIS was cooled to 4° C., and mixed with 10 ml of precooled buffer containing 0.2M $Na_2HPO_4$/0.09M NaOH. The solution was mixed at 4° C., and incubated at room temperature for about 16-20 hours, i.e., overnight, for convenience. The resulting collagen gel was then placed in a press and compressed using constant pressure of about 1.5 atmospheres to a flat collagen fiber network. The resulting network was dried in air at room temperature, washed with water, and redried in air. The resulting collagen membrane was designated G-1.

EXAMPLE 2.

90 ml of Zygen ® CIS at ambient temperature was mixed with 10 ml of room temperature buffer containing 0.2 M $Na_2HPO_4$/1.3M NaCl/0.09M NaOH, and the mixture incubated at 37° C. overnight. The resulting matrix was converted to a membrane as set forth in Example 1. The resulting membrane, G-2, is a smooth flexible translucent material. An electron micrograph of the fiber structure is shown in FIG. 1.

EXAMPLE 3.

Figure 2:
FIG. 2 is an electron micrograph at 30,000 times magnification of a membranous collagen produced by neutralizing cold collagen in solution with cold buffer, centrifuging, and incubating the supernatant to form a gel, and converting the gel to a membrane by compression under constant pressure.

90 ml of Zygen ® CIS was cooled to 4° C., and mixed rapidly with 10 ml cold (4° C.) buffer containing 0.2M $Na_2HPO_4$/0.09M NaOH, and transferred immediately to centrifuge bottles. The mixture was centrifuged at 8000×g for 2 hours at about 20° C., and the supernatant recovered from the bottles. The supernate was incubated at 20° C. for overnight, resulting in the gel. The gel was converted into the membrane in a manner exactly similar to that set forth Example 1, and designated G-3. An electron micrograph of the fiber structure is shown in FIG. 2.

EXAMPLE 4.

90 ml Zygen ® CIS and 10 ml insolubilizing buffer were mixed at 4° C., and incubated to form a gel exactly as set forth in Example 1. The gel matrix was broken with a spatula, transferred to a centrifuge bottle, and centrifuged at 13,000×g for 30 minutes. The resulting precipitate was recovered and homogenized into a paste form. The paste was cast into a mold and dried in air at 37° C., then washed with water and redried in air at 37° C. to give the membrane P-1.

EXAMPLE 5.

Zygen ® CIS was treated with buffer to form a gel exactly as described in Example 2, and the gel then converted to a membrane using the procedure exactly as set forth in Example 4. The resulting membrane was designated P-2.

EXAMPLE 6.

Zygen ® CIS was used to form a gel using the procedure as set forth in Example 3, and the resulting gel converted to a membrane as set forth in Example 4. The resulting membrane was designated P-3.

EXAMPLE 7.

90 ml Zygen ® CIS at ambient temperature was mixed with 10 ml buffer which contained 0.2M $Na_2HPO_4$/1.3M NaCl/0.09M NaOH, and the mixture incubated at 37° C. overnight. The resulting gel was compressed as set forth in Example 4, dried, and desalted by washing. The washed membrane was then cross-linked by treating with 0.1% glutaraldehyde dissolved in water at 20° C., and the cross-linked membrane washed and dried at low temperature to obtain membrane XG-2.

EXAMPLE 8.

A gel was formed from 90 ml Zygen ® CIS as described in Example 7, and the resulting gel broken with a spatula, transferred to a centrifuge bottle, and centrifuged at 13000×g for 30 minutes. The precipitate was recovered and homogenized to a paste. The paste was cast into a mold and dried in air at 37° C., and the resulting membrane washed with water. The washed membrane was then treated with a 0.1% solution of glutaraldehyde, as set forth in Example 7, and the cross-linked membrane washed and dried in to yield membrane XP-2.

EXAMPLE 9.

The procedure for gel formation as set forth in Example 2 was modified by de-gassing and molding the pre-gel mixture. Before incubation, the mixture was degassed by reduced pressure and placed in a mold. After incubation at 37° for 16-20 hours, the molded gelatin was compressed at about 1.5 atm to obtain a dense fiber network, which was dried in air at 37° or less. The dried solid was desalted by washing, re-molded, dried, and aged at an elevated temperature of about 40° C.-100° C. to increase residual cross-linking, to give the product designated "preformed G-2".

I claim:

1. A collagen membranous material which is prepared by raising the pH of a solution containing collagen to form a gel, followed by converting the gel to solid form, wherein said solid form constitutes a random fibrillar network wherein the fibrils are approximately of 70-300 nanometers diameter, and are approximately 0.5-5 microns in length.

2. The collagen material of claim 1 which is prepared from a solution of an atelopeptide collagen.

3. The collagen material of claim 1 which is cross-linked with glutaraldehyde.

4. The material of claim 1 wherein the solution of collagen contains atelopeptide collagen in a concentration of 2-4 mg/ml at pH about 2.

5. The material of claim 1 which is a two-dimensional membrane.

6. The collagen membranous material of claim 1 which is semi-transparent and has a rough surface texture.

7. The collagen membranous material of claim 1 which is flexible, translucent, smooth, and has high tensile strength.

* * * * *